US006852489B2

(12) United States Patent
Mori et al.

(10) Patent No.: US 6,852,489 B2
(45) Date of Patent: Feb. 8, 2005

(54) **SIMPLE AND QUICK METHOD FOR DETERMINING THE NUCLEOTIDE SEQUENCE OF A MITOCHONDRIAL 21S RIBOSOMAL RNA GENE OF YEAST BELONGING TO *SACCHAROMYCES CEREVISIAE***

(75) Inventors: Katsumi Mori, Iwate (JP); Takuma Gamou, Ibaraki (JP)

(73) Assignee: National Food Research Institute, Tsukuba (JP)

( * ) Notice: Subject to any disclaimer, the term of this patent is extended or adjusted under 35 U.S.C. 154(b) by 0 days.

(21) Appl. No.: 09/796,348

(22) Filed: Mar. 2, 2001

(65) Prior Publication Data

US 2002/0048757 A1 Apr. 25, 2002

(30) Foreign Application Priority Data

Sep. 21, 2000 (JP) ........................................ 2000-286748

(51) Int. Cl.⁷ ............................ C12Q 1/68; C12P 19/34; C07H 21/04
(52) U.S. Cl. ........................ 435/6; 435/91.2; 536/24.33
(58) Field of Search ................. 435/6, 91.2; 536/24.33, 536/22.1

(56) References Cited

U.S. PATENT DOCUMENTS 5,521,300 A * 5/1996 Shah et al. ............... 536/24.32
6,248,519 B1 * 6/2001 Engel et al. ................... 435/6

FOREIGN PATENT DOCUMENTS

WO        WO 01/32672 A1     5/2001

OTHER PUBLICATIONS

Dujon B. Sequence of the intron and flanking exons of mitochondrial 21S rRNA gene of yeast strains having different alleles at the w and rib–1 loci. Cell, vol. 20: 185–197, 1980.*

Jacquier et al. The intron of the mitochondrial 21S rRNA gene: Distribution in different yeast species and sequence comparison between *Kluyveromyces thermotolerans* and *Saccharomyces cerevisiae*. Mol.Gen.Genet., vol. 192: 487–499, 1983.*

Dujon B. Sequence of the intron and flanking exons of mitochondrial 21S rRNA gene of Yeast strains having different alleles at the w and rib–1 loci. Cell, vol. 20: 185–197, 1980.*

Sor et al. Complete DNA sequence coding for the large ribosomal RNA of yeast mitochondria. Nucleic Acids Res., vol. 11 (2), pp. 339–348, 1983.*

Jacquier et al. The intron of the mitochondrial 21S rRNA gene: distribution in different yeast species and sequence comparison between *Kluyveromyces thermotolerans* and *Saccharomyces cerevisiae*. Mol. Gen. Genet., Vo. 192, pp. 487–499, 1983.*

Dujon B. Sequence of the intron and flanking exons of mitochondrial 21S rRNA gene of yeast strains having different alleles at the w and rib–1 loci. Cell, vol. 20, pp. 185–197, 1980.*

Buck et al. Design strategies and performance of custom DNA sequencing primers. Biotechniques, vol. 27, No. 3, pp. 528–536, 1999.*

S. Donhauser et al., Monatsschrift Fuer Brauwissenschaft, vol. 42, No. 1, 1989, pp. 4–10.

C. Atzori et al., International Journal of Infectious Diseases, vol. 3, No. 2, 1998, pp. 76–81.

E. Rinyu et al., Journal of Clinical Microbiology, vol. 33, No. 10, 1996, pp. 2567–2575.

Z. Shen et al., Helicobacter, vol. 5, No. 3, 2000, pp. 121–128.

Kelly, R. et al., Molecular and Cellular Biology, vol. 3, No. 11, pp. 1949–1957 (1983).

* cited by examiner

*Primary Examiner*—Jeffrey Fredman
*Assistant Examiner*—Suryaprabha Chunduru
(74) *Attorney, Agent, or Firm*—Birch, Stewart, Kolasch & Birch, LLP

(57) ABSTRACT

The present invention provides a simple and quick method for determining the nucleotide sequence of the mitochondrial 21S ribosomal RNA gene of *Saccharomyces cerevisiae* by gene amplification technique, and a method for classifying *Saccharomyces cerevisiae* strains using the same nucleotide sequence. To achieve this object, the mitochondrial 21S ribosomal RNA gene of *Saccharomyces cerevisiae* is amplified by gene amplification technique, thereby determining the nucleotide sequence of the gene.

3 Claims, 8 Drawing Sheets

Lane 1 2 3 4 5 6 7 8

FIG.2

```
MT21S-I-1*)
  -413F**): CAAAATAGTCCGACCGAAGGAGATGAG
   461R: CTTGCTGACCCATTATACAAAAGGTAC
MT21S-I-2
    64F: AGATTTAAAGAGATAATCATGGAG
   690R: ATAGAAAACCAGCTATCTGC
MT21S-II
   478F: GTACCTTTTGTATAATGG
  1290R: CGTTACTCATGTCAGCATTC
MT21S-III
  1048F: ATGAACATGTAACAATGCACTG
  1615R: CTAACTTATGAGCTATCTTTGCCGAG
MT21S-IV
  1590F: CAGGTATGTAAGTAGAGAATATGAAGGTG
  2258R: CTGATAATGACGCCCATCAAAACTAC
MT21S-V
  1945F: AGTGAAGATGCTATGTACCTTCAGCAAG
  [2269F: CAATCTCTAATTGGTAGTTTTGATG]
  2676R: CTAGCGTAACTTTTATTCGTTATCAATAACC
MT21S-VI
  2624F: CGAGTGAAACAAGTACGTAAGTATGGC
  [3889F: TAAGCT(A/C)TGTTTG(C/A)CACCTCGATGTCG]
  4457R: ATAAAGGTGTGAACCAATCCCGCAAGG
```

FIG.3A

```
                        10         20         30         40         50
IFO 10217     1  TAGTAAAAAG TAGAATAATA GGTTTGAAAT ATTTATTATA TAGATTTAAA    50
IFO 10055     1  TAGTAAAAAG TAGAATAATA GATTTGAAAT ATTTATTATA TAGATTTAAA    50
IFO 1998      1  TAGTAAAAAG TAGAATAATA GATTTGAAAT ATTTATTATA TAGATTTAAA    50

60         70         80         90        100
IFO 10217    51  GAGATAATCA TGGAGTATAA AAATTAAATT TAATAAATTT AATATAACTA   100
IFO 10055    51  GAGATAATCA TGGAGTATAA AAATTAAATT TAATAAATTT AATATAACTA   100
IFO 1998     51  GAGATAATCA TGGAGTATAA AAATTAAATT TAATAAATTT AATATAACTA   100

110        120        130        140        150
IFO 10217   101  TTAATAGAAT TAGGTTACTA ATAAATTAAT AACAATTAAT TTTAAAACCT   150
IFO 10055   101  TTAATAGAAT TAGGTTACTA ATAAATTAAT AACAATTAAT TTTAAAACCT   150
IFO 1998    101  TTAATAGAAT TAGGTTACTA ATAAATTAAT AACAATTAAT TTTAAAACCT   150

160        170        180        190        200
IFO 10217   151  AAAGGTAAAG CTTTATATTA ATAATGTTTT TTTTT---AT TTTTATAATT   200
IFO 10055   151  AAAGGTAAAG CTTTATATTA ATAATGTTTT TTTTT-TAAT TTTTATAATT   200
IFO 1998    151  AAAGGTAAAG CTTTATATTA ATAATGTTTT TTTTTTTAT TTTTATAATT    200

210        220        230        240        250
IFO 10217   201  AAGAATAATT ATTAATAATA ATAAACTAAG TGAACTGAAA CATCTAAGTA   250
IFO 10055   201  AAGAATAATT ATTAATAATA ATAAACTAAG TGAACTGAAA CATCTAAGTA   250
IFO 1998    201  AAGAATAATT ATTAATAATA ATAAACTAAG TGAACTGAAA CATCTAAGTA   250

260        270        280        290        300
IFO 10217   251  ACTTAAGGAT AATAAATCAA CAGAGATATT ATGAGTATTG GTGAGAGAAA   300
IFO 10055   251  ACTTAAGGAT AATAAATCAA CAGAGATATT ATGAGTATTG GTGAGAGAAA   300
IFO 1998    251  ACTTAAGGAT AATAAATCAA CAGAGATATT ATGAGTATTG GTGAGAGAAA   300

310        320        330        340        350
IFO 10217   301  ATAATAAAGG TCTAATAAGT ATTATGTGAA AAAAATGTAA GAAAATAGGA   350
IFO 10055   301  ATAATATAGG TGAATAAGT ATTATGTGAA AAAATGTAA GAAAATAGGA     350
IFO 1998    301  ATAATAAAGG TCTAATAAGT ATTATGTGAA AAAAATGTAA GAAAATAGGA   350

360        370        380        390        400
IFO 10217   351  TAACAAATTG TAAGACTAAA TACTATTAAT AAGTATAGTA AGTACCGTAA   400
IFO 10055   351  TAACAAATTC TAAGACTAAA TACTATTAAT AAGTATAGTA AGTACCGTAA   400
IFO 1998    351  TAACAAATTC TAAGACTAAA TACTATTAAT AAGTATAGTA AGTACCGTAA   400

410        420        430        440        450
IFO 10217   401  GGGAAAGTAT GAAAATGATT ATTTTATAAG CAATCATGAA TATATTATAT   450
IFO 10055   401  GGGAAAATAT GAAAATGATT ATTTTATAAG CAATCATGAA TATATTATAT   450
IFO 1998    401  GGGAAAATAT GAAAATGATT ATTTTATAAG CAATCATGAA TATATTATAT   450

460        470        480        490        500
IFO 10217   451  TATATTAATG ATGTACCTTT TGTATAATGG GTCAGCAAGT AATTAATATT   500
IFO 10055   451  TATATTAATG ATGTACCTTT TGTATAATGG GTCAGCAAGT AATTAATATT   500
IFO 1998    451  TATATTAATG ATGTACCTTT TGTATAATGG GTCAGCAAGT AATTAATATT   500

510        520        530        540        550
IFO 10217   501  AGTAAAACAA TAAGTTATAA ATAAATAGAA TAATATATAT ATATAAAAAA   550
IFO 10055   501  AGTAAAACAA TAAGTTATAA ATAAATAGAA TAATATATAT ATATAAAAAA   550
IFO 1998    501  AGTAAAACAA TAAGTTATAA ATAAATAGAA TAATATATAT ATATAAAAAA   550

560        570        580        590        600
IFO 10217   551  ATATATTAAA ATATTTAATT AATATTAATT GACCCGAAAG CAAACGATCT   600
IFO 10055   551  ATATATTAAA ATATTTAATT AATATTAATT GACCCGAAAG CAAACGATCT   600
IFO 1998    551  ATATATTAAA ATATTTAATT AATATTAATT GACCCGAAAG CAAACGATCT   600

610        620        630        640        650
IFO 10217   601  AACTATGATA AGATGGATAA ACGATCGAAC AGGTTGATGT TGCAATATCA   650
IFO 10055   601  AACTATGATA AGATGGATAA ACGATCGAAC AGGTTGATGT TGCAATATCA   650
IFO 1998    601  AACTATGATA AGATGGATAA ACGATCGAAC AGGTTGATGT TGCAATATCA   650

660        670        680        690        700
IFO 10217   651  TCTGATTAAT TGTGGTTAGT AGTGAAAGAC AAATCTGGTT TGCAGATAGC   700
IFO 10055   651  TCTGATTAAT TGTGGTTAGT AGTGAAAGAC AAATCTGGTT TGCAGATAGC   700
IFO 1998    651  TCTGATTAAT TGTGGTTAGT AGTGAAAGAC AAATCTGGTT TGCAGATAGC   700
```

FIG. 3B

```
                    710        720        730        740        750
IFO 10217    701  TGGTTTCTA  TGAAATATAT  GTAAGTATAG  CCTTTATAAA  TAATAATTAT   750
IFO 10055    701  TGGTTTCTA  TGAAATATAT  GTAAGTATAG  CCTTTATAAA  TAATAATTAT   750
IFO 1998     701  TGGTTTCTA  TGAAATATAT  GTAAGTATAG  CCTTTATAAA  TAATAATTAT   750

760        770        780        790        800
IFO 10217    751  TATATAATAT  TATATAAATA  TTATATAAAG  AATGGTACAG  CAATTAATAT   800
IFO 10055    751  TATATAATAT  TATATAAATA  TTATATAAAG  AATGGTACAG  CAATTAATAT   800
IFO 1998     751  TATATAATAT  TATATAAATA  TTATATAAAG  AATGGTACAG  CAATTAATAT   800

810        820        830        840        850
IFO 10217    801  ATATTAGGGA  ACTATTAAAG  TTTTATTAAT  AATATTAAAT  CTCGAAATAT   850
IFO 10055    801  ATATTAGGGA  ACTATTAAAG  TTTTATTAAT  AATATTAAAT  CTCGAAATAT   850
IFO 1998     801  ATATTAGGGA  ACTATTAAAG  TTTTATTAAT  AATATTAAAT  CTCGAAATAT   850

860        870        880        890        900
IFO 10217    851  TTAATTATAT  ATAATAAAGA  GTCAGATTAT  GTGCGATAAG  GTAAATAATC   900
IFO 10055    851  TTAATTATAT  ATAATAAAGA  GTCAGATTAT  GTGCGATAAG  GTAAATAATC   900
IFO 1998     851  TTAATTATAT  ATAATAAAGA  GTCAGATTAT  GTGCGATAAG  GTAAATAATC   900

910        920        930        940        950
IFO 10217    901  TAAAGGGAAA  CAGCCCAGAT  TAAGATATAA  AGTTCCTAAT  AAATAATAAG   950
IFO 10055    901  TAAAGGGAAA  CAGCCCAGAT  TAAGATATAA  AGTTCCTAAT  AAATAATAAG   950
IFO 1998     901  TAAAGGGAAA  CAGCCCAGAT  TAAGATATAA  AGTTCCTAAT  AAATAATAAG   950

960        970        980        990       1000
IFO 10217    951  TGAAATAAAT  ATTAAAATAT  TATAATATAA  TCAGTTAATG  GGTTTGACAA  1000
IFO 10055    951  TGAAATAAAT  ATTAAAATAT  TATAATATAA  TCAGTTAATG  GGTTTGACAA  1000
IFO 1998     951  TGAAATAAAT  ATTAAAATAT  TATAATATAA  TCAGTTAATG  GGTTTGACAA  1000

1010       1020       1030       1040       1050
IFO 10217   1001  TAACCATTTT  TTAATGAACA  TGTAACAATG  CACTGATTTA  TAATAAATAA  1050
IFO 10055   1001  TAACCATTTT  TTAATGAACA  TGTAACAATG  CACTGATTTA  TAATAAATAA  1050
IFO 1998    1001  TAACCATTTT  TTAATGAACA  TGTAACAATG  CACTGATTTA  TAATAAATAA  1050

1060       1070       1080       1090       1100
IFO 10217   1051  AAAAAAATAA  TATTTAAAAT  CAAATATATA  TATATTTGTT  AATAGATAAT  1100
IFO 10055   1051  AAAAAAATAA  TATTTAAAAT  CAAATATATA  TATATTTGTT  AATAGATAAT  1100
IFO 1998    1051  AAAAAAATAA  TATTTAAAAT  CAAATATATA  TATATTTGTT  AATAGATAAT  1100

1110       1120       1130       1140       1150
IFO 10217   1101  ATACGGATCT  TAATAATAAG  AATTATTTAA  TTCCTAATAT  GGAATATTAT  1150
IFO 10055   1101  ATACGGATCT  TAATAATAAG  AATTATTTAA  TTCCTAATAT  GGAATATTAT  1150
IFO 1998    1101  ATACGGATCT  TAATAATAAG  AATTATTTAA  TTCCTAATAT  GGAATATTAT  1150

1160       1170       1180       1190       1200
IFO 10217   1151  ATTTTTATAA  TAATAATAAG  AATATAAATA  CTGAATATCT  AAATATTATT  1200
IFO 10055   1151  ATTTTTATAA  TAATAATAAG  AATATAAATA  CTGAATATCT  AAATATTATT  1200
IFO 1998    1151  ATTTTTATAA  TAATAATAAA  AATATAAATA  CTGAATATCT  AAATATTATT  1200

1210       1220       1230       1240       1250
IFO 10217   1201  ATTACTTTTT  TTTTAATAAT  AATAATATGG  TAATAGAACA  TTTAATGATA  1250
IFO 10055   1201  ATTACTTTTT  TTT-AATAAT  AATAATATGG  TAATAGAACA  TTTAATGATA  1250
IFO 1998    1201  ATTACTTTTT  TT--AATAAT  AATAATATGG  TAATAGAACA  TTTAATGATA  1250

1260       1270       1280       1290       1300
IFO 10217   1251  ATATATATTA  GTTATTAATT  AATATATGTA  TTAATTAAAT  AGAGAATGCT  1300
IFO 10055   1251  ATATATATTA  GTTATTAATT  AATATATGTA  TTAATTAAAT  AGAGAATGCT  1300
IFO 1998    1251  ATATATATTA  GTTATTAATT  AATATATGTA  TTAATTAAAT  AGAGAATGCT  1300

1310       1320       1330       1340       1350
IFO 10217   1301  GACATGAGTA  ACGAAAAAAA  GGTATAAACC  TTTTCACCTA  AAACATAAGG  1350
IFO 10055   1301  GACATGAGTA  ACGAAAAAAA  GGTATAAACC  TTTTCACCTA  AAACATAAGG  1350
IFO 1998    1301  GACATGAGTA  ACGAAAAAAA  GGTATAAACC  TTTTCACCTA  AAACATAAGG  1350

1360       1370       1380       1390       1400
IFO 10217   1351  TTTAACTATA  AAAGTACGGC  CCCTAATTAA  ATTATATAAG  AATATAAATA  1400
IFO 10055   1351  TTTAACTATA  AAAGTACGGC  CCCTAATTAA  ATTATATAAG  AATATAAATA  1400
IFO 1998    1351  TTTAACTATA  AAAGTACGGC  CCCTAATTAA  ATTATATAAG  AATATAAATA  1400
```

FIG.3C

```
                    1410       1420       1430       1440       1450
IFO 10217  1401 TATTTAAGAT GGGATAATCT ATATTAATAA AAATTTATCT TAAAATATAT  1450
IFO 10055  1401 TATTTAAGAT GGGATAATCT ATATTAATAA AAATTTATCT TAAAATATAT  1450
IFO 1998   1401 TATTTAAGAT GGGATAATCT ATATTAATAA AAATTTATCT TAAAATATAT  1450

1460       1470       1480       1490       1500
IFO 10217  1451 ATATTATTAA TAATTATATT AATTAATTAA TAATATATAT AATTATATTA  1500
IFO 10055  1451 ATATTATTAA TAATTATATT AATTAATTAA TAATATATAT AATTATATTA  1500
IFO 1998   1451 ATATTATTAA TAATTATATT AATTAATTAA TAATATATAT AATTATATTA  1500

1510       1520       1530       1540       1550
IFO 10217  1501 TATATTATAT TTTTATATAT AATATATATA ATATAAACTA ATAAAGATCA  1550
IFO 10055  1501 TATATTATAT TTTTATATAT AATATATATA ATATAAACTA ATAAAGATCA  1550
IFO 1998   1501 TATATTATAT TTTTATATAT AATATATATA ATATAAACTA ATAAAGATCA  1550

1560       1570       1580       1590       1600
IFO 10217  1551 GGAAATAATT AATGTATACC GTAATGTAGA CCGACTCAGG TATGTAAGTA  1600
IFO 10055  1551 GGAAATAATT AATGTATACC GTAATGTAGA CCGACTCAGG TATGTAAGTA  1600
IFO 1998   1551 GGAAATAATT AATGTATACC GTAATGTAGA CCGACTCAGG TATGTAAGTA  1600

1610       1620       1630       1640       1650
IFO 10217  1601 GAGAATATGA AGGTGAATTA GATAATTAAA GGGAAGGAAC TCGGCAAAGA  1650
IFO 10055  1601 GAGAATATGA AGGTGAATTA GATAATTAAA GGGAAGGAAC TCGGCAAAGA  1650
IFO 1998   1601 GAGAATATGA AGGTGAATTA GATAATTAAA GGGAAGGAAC TCGGCAAAGA  1650

1660       1670       1680       1690       1700
IFO 10217  1651 TAGCTCATAA GTTAGTCAAT AAAGAGTAAT AAGAACAAAG TTGTACAACT  1700
IFO 10055  1651 TAGCTCATAA GTTAGTCAAT AAAGAGTAAT AAGAACAAAG TTGTACAACT  1700
IFO 1998   1651 TAGCTCATAA GTTAGTCAAT AAAGAGTAAT AAGAACAAAG TTGTACAACT  1700

1710       1720       1730       1740       1750
IFO 10217  1701 GTTTACTAAA AACACCGCAC TTTGCAGAAA CGATAAGTTT AAGTATAAGG  1750
IFO 10055  1701 GTTTACTAAA AACACCGCAC TTTGCAGAAA CGATAAGTTT AAGTATAAGG  1750
IFO 1998   1701 GTTTACTAAA AACACCGCAC TTTGCAGAAA CGATAAGTTT AAGTATAAGG  1750

1760       1770       1780       1790       1800
IFO 10217  1751 TGTGAACTCT GCTCCATGCT TAATATATAA ATAAAATTAT TTAACGATAA  1800
IFO 10055  1751 TGTGAACTCT GCTCCATGCT TAATATATAA ATAAAATTAT TTAACGATAA  1800
IFO 1998   1751 TGTGAACTCT GCTCCATGCT TAATATATAA ATAAAATTAT TTAACGATAA  1800

1810       1820       1830       1840       1850
IFO 10217  1801 TTTTATTAAA TTTAGGTAAA TAGCAGCCTT ATTATGAGGG TTATAATGTA  1850
IFO 10055  1801 TTTTATTAAA TTTAGGTAAA TAGCAGCCTT ATTATGAGGG TTATAATGTA  1850
IFO 1998   1801 TTTTATTAAA TTTAGGTAAA TAGCAGCCTT ATTATGAGGG TTATAATGTA  1850

1860       1870       1880       1890       1900
IFO 10217  1851 GCGAATTCG TTGGGCTATA ATTGAGGTCG CGCATGAATG ACGTAATGAT  1900
IFO 10055  1851 GCGAATTCG TTGGGCTATA ATTGAGGTCG CGCATGAATG ACGTAATGAT  1900
IFO 1998   1851 GCGAATTCG TTGGGCTATA ATTGAGGTCG CGCATGAATG ACGTAATGAT  1900

1910       1920       1930       1940       1950
IFO 10217  1901 ACAACAACTG TCTCCCCTTT AAGCTAAGTG AAATTGAAAT CGTAGTGAAG  1950
IFO 10055  1901 ACAACAACTG TCTCCCCTTT AAGCTAAGTG AAATTGAAAT CGTAGTGAAG  1950
IFO 1998   1901 ACAACAACTG TCTCCCCTTT AAGCTAAGTG AAATTGAAAT CGTAGTGAAG  1950

1960       1970       1980       1990       2000
IFO 10217  1951 ATGCTATGTA CCTTCAGCAA GACGGAAAGA CCCTATGCAG CTTTACTGTA  2000
IFO 10055  1951 ATGCTATGTA CCTTCAGCAA GACGGAAAGA CCCTATGCAG CTTTACTGTA  2000
IFO 1998   1951 ATGCTATGTA CCTTCAGCAA GACGGAAAGA CCCTATGCAG CTTTACTGTA  2000

2010       2020       2030       2040       2050
IFO 10217  2001 ATTAGATAGA TCGAATTATT GTTTATTATA TTCAGCATAT TAAGTAATCC  2050
IFO 10055  2001 ATTAGATAGA TCGAATTATT GTTTATTATA TTCAGCATAT TAAGTAATCC  2050
IFO 1998   2001 ATTAGATAGA TCGAATTATT GTTTATTATA TTCAGCATAT TAAGTAATCC  2050

2060       2070       2080       2090       2100
IFO 10217  2051 TATTATTAGG TAATCGTTTA GATATTAATG AGATACTTAT TATAATATAT  2100
IFO 10055  2051 TATTATTAGG TAATTGTTTA GATATTAATG AGATACTTAT TATAATATAA  2100
IFO 1998   2051 TATTATTAGG TAATCGTTTA GATATTAATG AGATACTTAT TATAATATAA  2100
```

FIG.3D

```
              2110       2120       2130       2140       2150
IFO 10217  2101 TGATAATTCT AATCTTATAA ATAATTATTA TTATTATTAT TAATAATAAT
IFO 10055  2101 TGATAATTCT AATCTTATAA ATAATTATTA TTATTATTAT TAATAATAAT  2150
IFO 1998   2101 TGATAATTCT AATCTTATAA ATAATTATTA TTATTATTAT TAATAATAAT  2150
                                                                        2150

2160       2170       2180       2190       2200
IFO 10217  2151
IFO 10055  2151                                                         2200
IFO 1998   2151                                                         2200
                                                                        2200

2210       2220       2230       2240       2250
IFO 10217  2201
IFO 10055  2201                                                         2250
IFO 1998   2201                                                         2250
                                                                        2250

2260       2270       2280       2290       2300
IFO 10217  2251
IFO 10055  2251                                                         2300
IFO 1998   2251                                                         2300
                                                                        2300

2310       2320       2330       2340       2350
IFO 10217  2301
IFO 10055  2301                                                         2350
IFO 1998   2301                                                         2350
                                                                        2350

2360       2370       2380       2390       2400
IFO 10217  2351
IFO 10055  2351                                                         2400
IFO 1998   2351                                                         2400
                                                                        2400

2410       2420       2430       2440       2450
IFO 10217  2401
IFO 10055  2401                                                         2450
IFO 1998   2401                                                         2450
                                                                        2450

2460       2470       2480       2490       2500
IFO 10217  2451
IFO 10055  2451                                                         2500
IFO 1998   2451                                                         2500
                                                                        2500

2510       2520       2530       2540       2550
IFO 10217  2501 CGGTGGGGGT TCACACGTAT TTTTAATAGG TGTGAACCCG TC--------
IFO 10055  2501 CGGTGGGGGT TGACAGGTAT TTTTAATAGG TGTGAACGCG TCTTCGGGGT  2550
IFO 1998   2501 CGGTGGGGGT TCACACCTAT TTTTAATAGG TGTGAACCCG TCTTCGGGGT  2550
                                                                        2550

2560       2570       2580       2590       2600
IFO 10217  2551 ---------- ---------- -----GTTAA AAAATAAAA TGGAAAGTAT
IFO 10055  2551                                  ---TAAAA TGTAAAGAAT   2600
IFO 1998   2551                                  A---TAAAA TGGAAAGAAT   2600
                                                                        2600

2610       2620       2630       2640       2650
IFO 10217  2601 TAAATTAATA TAATGGTATA ACTGTGCGAT AATTGTAAGA CAAACGAGTG
IFO 10055  2601 TAAATTAATA TAATGGTATA ACTGTGCGAT AATTGTAAGA CAAACGACTG  2650
IFO 1998   2601 TAAATTAATA TAATGGTATA ACTGTGGGAT AATTGTAAGA CAAACGAGTG  2650
                                                                        2650

2660       2670       2680       2690       2700
IFO 10217  2651 AAACAAGTAC GTAAGTATGG CATAATGAAC AAATAACACT GATTGTAAAG
IFO 10055  2651 AAAEAAGTAG GTAAGTATGG CATAATGAAC AAATAACACT GATTGTAAAG  2700
IFO 1998   2651 AAACAAGTAC GTAAGTATGG CATAATGAAC AAATAACACT GATTGTAAAG  2700
                                                                        2700

2710       2720       2730       2740       2750
IFO 10217  2701 GTTATTGATA ACGAATAAAA GTTACGCTAG GGATAACAGG GTAATATAAC
IFO 10055  2701 GTTATTGATA ACGAATAAAA GTTACGCTAG GGATAACAGG GTAATATAAC  2750
IFO 1998   2701 GTTATTGATA ACGAATAAAA GTTACGCTAG GGATAACAGG GTAATATAAC  2750
                                                                        2750

2760       2770       2780       2790       2800
IFO 10217  2751 GAAAGAGTAG ATATTGTAAG TTATGTTTGC CACCTCGATG TCGACTCAAC
IFO 10055  2751 GAAAGAGTAG ATATTGTAAG TTATGTTTGC CACCTCGATG TCGACTCAAC  2800
IFO 1998   2751 GAAAGAGTAG ATATTGTAAG TTATGTTTGC CACGTCGATG TCGACTCAAC  2800
                                                                        2800
```

FIG.3E

```
               2810       2820       2830       2840       2850
IFO 10217  2801 ATTTCCTCTT GGTTGTAAAA GCTAAGAAGG GTTTGACTGT TCGTCAATTA  2850
IFO 10055  2801 ATTTCCTCTT GGTTGTAAAA GCTAAGAAGG GTTTGACTGT TCGTCAATTA  2850
IFO 1998   2801 ATTTCCTCTT GGTTGTAAAA GCTAAGAAGA GTTTGACTGT TCGTCAATTA  2850

2860       2870       2880       2890       2900
IFO 10217  2851 AAATGTTAGG TGAGTTGGTT TAAATACTAT GTGATTGAGT ATGGTTGGAA  2900
IFO 10055  2851 AAATGTTAGG TGAGTTGGTT TAAATACTAT GTGATTGAGT ATGGTTGGAA  2900
IFO 1998   2851 AAATGTTAGG TGAGTTGGTT TAAATACTAT GTGATTGAGT ATGGTTGGAA  2900

2910       2920       2930       2940       2950
IFO 10217  2901 TCTCGCTTAA AAATATTAAT AATAATAATT CTGATTAATTA GTATGGATTG  2950
IFO 10055  2901 TCTCGCTTAA AAATATTAAT AATAATAATT CTGATTAATTA GTATGGATTG  2950
IFO 1998   2901 TCGCGCTTAA AAATATTAAT AATAATAATT CTGATTAATTA TTACGGAATG  2950

2960       2970       2980       2990       3000
IFO 10217  2951 ACCATAATGA ATCAAGGCAT GGTCTATCTA TTGATAATAA TATAATATAT  3000
IFO 10055  2951 ACCATAATGA ATCAAGGCAT GGTCTATCTA TTGATAATAA TATAATATAT  3000
IFO 1998   2951 ACCATAATGA ATCAAGGCAT GGTCTATCTA TTGATAATAA TATAATATAT  3000

3010       3020       3030       3040       3050
IFO 10217  3001 TTAATAAAAA TAATACTTTA TTAATATATT ATCTATATTA CTTTATATTT  3050
IFO 10055  3001 TTAATAAAAA TAATACTTTA TTAATATATT ATGTATATTA CTTTATATTT  3050
IFO 1998   3001 TTAATAAAAA TAATACTTTA TTAATATATT ATCTATATTA CTTTATATTT  3050

3060       3070       3080       3090       3100
IFO 10217  3051 TAATTATATA TTATCATAAT AGATAAGCTA AGTTGATAAT AAATAAATAT  3100
IFO 10055  3051 TAATTATATA TTATCATAGT AGATAAGCTA AGTTGATAAT AAATAAATAT  3100
IFO 1998   3051 TAATTATATA TTATCATAGT AGATAAGCTA AGTTGATAAT AAATAAATAT  3100

3110       3120       3130       3140       3150
IFO 10217  3101 TGAATACATA TTAAATATGA AGTTGTTTTA ATAAGATAAT TAATCTGATA  3150
IFO 10055  3101 TGAATACATA TTAAATATGA AGTTGTTTTA ATAAGATAAT TAATCTGATA  3150
IFO 1998   3101 TGAATACATA TTAAATATGA AGTTGTTTTA ATAAGATAAT TAATCTGATA  3150

3160       3170       3180       3190       3200
IFO 10217  3151 ATTTCATAGT AAATTAAATA ATTATAGTTA TTATATATTA TTTATAAA--  3200
IFO 10055  3151 ATTTCATAGT AAATTAAATA ATTATAGTTA TTATATATTA TTTATAAATA  3200
IFO 1998   3151 ATTTCATAGT AAATTAAATA ATTATAGTTA TTATATATTA TTTATAAA--  3200

3210       3220       3230       3240       3250
IFO 10217  3201 -------TAT AATA-TAATA ATTATATTA TTAA---TAA AAAAATATAT  3250
IFO 10055  3201 AATATAATAT AATA-TAATA ATTATATTA TTAA---TAA AAAAATATA   3250
IFO 1998   3201 -------TAT AATA-TAATA ATTATATTA TTAA---TAA AAAAATATA   3250

3260       3270       3280       3290       3300
IFO 10217  3251 TAATTATAAT ATTAATAAAA TACTAATTTA TCAGTTATCT ATATAATATC  3300
IFO 10055  3251 TAATTATAAT ATTAATAAAA TACTAATTTA TCAGTTATCT ATATAATATC  3300
IFO 1998   3251 TAATTATAAT ATTAATAAAA TACTAATTTA TCAGTTATCT ATATAATATC  3300

3310       3320       3330       3340       3350
IFO 10217  3301 TAATCTATTA TTCTATATAC ..........  ..........  ..........  3350
IFO 10055  3301 TAATCTATTA TTCTATATAC ..........  ..........  ..........  3350
IFO 1998   3301 TAATCTATTA TTCTATATAC ..........  ..........  ..........  3350
```

SIMPLE AND QUICK METHOD FOR DETERMINING THE NUCLEOTIDE SEQUENCE OF A MITOCHONDRIAL 21S RIBOSOMAL RNA GENE OF YEAST BELONGING TO *SACCHAROMYCES CEREVISIAE*

FIELD OF THE INVENTION

The present invention relates to a simple and quick method for determining the nucleotide sequence of a mitochondrial 21S ribosomal RNA gene of yeast belonging to *Saccharomyces cerevisiae* and a method for classifying *Saccharomyces cerevisiae* strains using the same nucleotide sequence.

BACKGROUND OF THE INVENTION

*Saccharomyces cerevisiae* comprises various strains, of which each has differing properties. So, there are many strains which had previously been reported as different species from *Saccharomyces cerevisiae*, but then were determined to belong to this species (C. P. Kurtzman and J. W. Fell: *The Yeasts, A taxonomic study*, 4th ed. Elsevier, The Netherlands, 1998). Since strains belonging to *Saccharomyces cerevisiae* are frequently used for the production of various fermented food or alcoholic beverages, the instability of the classification system of *Saccharomyces cerevisiae* strains presents problems, causing confusion at the site of study or production.

Although a subclassification on the basis of the requirement of vitamins has been carried out up till now (Tatsuyoshi Yamaguchi: "A study regarding the classification of baker's yeast (the 6th publication), the classification of baker's yeast in each country", *Biosci. Biotech. Biochem.*, vol.33, p. 513–519, 1959), the analysis of the strains was difficult.

In recent years, however, the development of molecular phylogeny mainly regarding bacteria, which uses ribosomal RNA molecules, has allowed microorganisms including bacteria to be phylogenetically classified. Yeast belonging to fungus can also be phylogenetically classified by making a comparison of cytoplasmic ribosomal RNA or the nucleotide sequence of the gene. However, since there are very few mutations in the nucleotide sequences of cytoplasmic ribosomal RNAs, it is considered that the cytoplasmic ribosomal RNA is not suitable for the phyloanalysis of allied strains.

SUMMARY OF THE INVENTION

Considering the above-described situation, the present inventors have focused attention on a mitochondrial ribosomal RNA gene which has more mutations than does cytoplasmic ribosomal RNA, and have intended to use this to carry out the phyloanalysis of allied strains, thereby completing the present invention. That is to say, the object of the present invention is to provide a simple and quick method for determining the nucleotide sequence of a mitochondrial 21S ribosomal RNA gene of *Saccharomyces cerevisiae* by gene amplification technique, and a method for classifying *Saccharomyces cerevisiae* strains using the same nucleotide sequence.

The present invention relates to a method for determining the nucleotide sequence of a mitochondrial 21S ribosornal RNA gene of *Saccharomyces cerevisiae*, wherein a mitochondrial 21S ribosomal RNA gene of *Saccharomyces cerevisiae* is amplified by a gene amplification technique to determine the nucleotide sequence of the above gene.

Primers used for the above gene amplification technique are shown in SEQ ID NOS: 1 to 16.

Furthermore, the present invention relates to a method for classifying *Saccharomyces cerevisiae* strains, wherein *Saccharomyces cerevisiae* strains are classified using the nucleotide sequence of the mitochondrial 21S ribosomal RNA gene of *Saccharomyces cerevisiae*.

Figure 1:
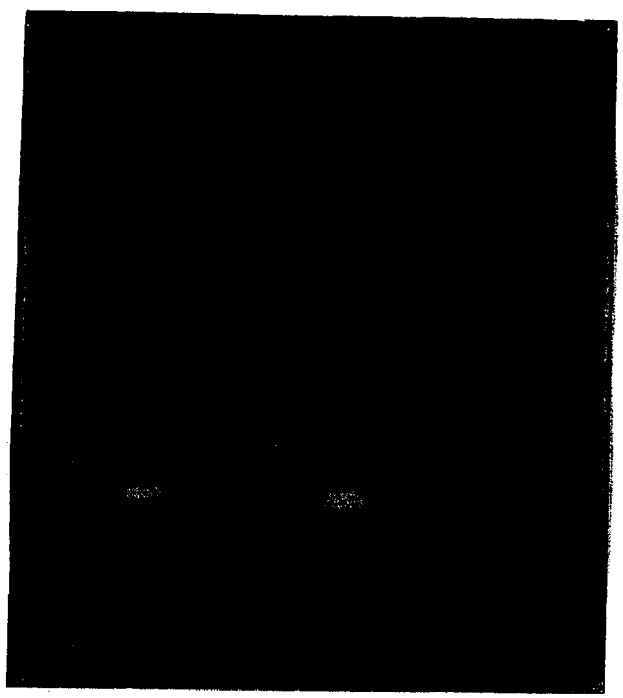
FIG. 1 shows the electrophoresis image of the mitochondrial 21S ribosomal RNA gene of *Saccharomyces cerevisiae* amplified by PCR.

Electrophoresis image of the mitochondrial 21 S ribosomal RNA gene of *Saccharomyces cerevisiae* which was amplified by PCR (lane 1; PCR product obtained using primers −413F and 461R, lane 2; PCR product obtained using primers 64F and 960R, lane 3; PCR product obtained using primers 478F and 1290R, lane 4; a marker, lane 5; PCR product obtained using 1048F and 1615R, lane 6; PCR product obtained using primers 1590F and 2258R, lane 7; PCR product obtained using primers 1945F and 2676R, lane 8; PCR product obtained using primers 2624F and 4457R).

FIG. 2 shows primers used for PCR on Mt-21S rRNA gene of *Saccharomyces cerevisiae*.

Primers used for PCR on Mt-21S rRNA gene of *Saccharomyces cerevisiae*
*) Names of primer combinations
**) Names of primers
Loci described in ( )are dibasic mixes
Primers described in [ ] are specific for the determination of nucleotide sequence.

FIG. 3 is a diagram showing homology between each Mt-21S rRNA gene of 3 stains of *Saccharomyces cerevisiae*.

Alignment of mitochondrial 21S ribosomal RNA gene nucleotide sequences of 3 strains belonging to *Saccharomyces cerevisiae* (A; adenine, C; cytosine, G; guanine, T; thymine, Y; C or T, -; no nucleotide, shaded parts; parts wherein the nucleotide sequences in more than 2 strains match).

Figure 4:
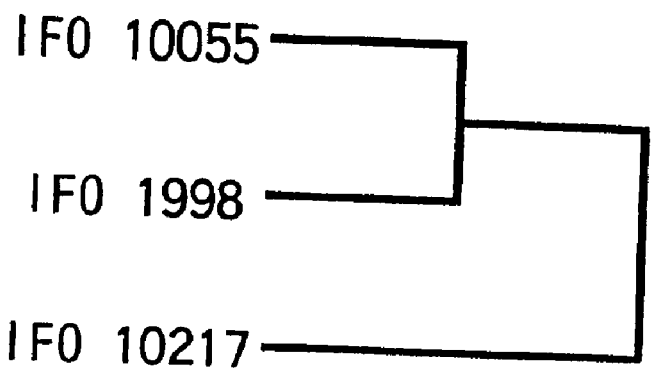

FIG. 4 is a dendrogram created on the basis of homology between each Mt-21S rRNA gene of 3 stains of *Saccharomyces cerevisiae*.

Dendrogram showing the phylogenic relation between three strains of *Saccharomyces cerevisiae*, which was made utilizing the nucleotide sequence of mitochondrial 21 S ribosomal RNA gene.

DETAILED DESCRIPTION OF THE INVENTION

The present invention is described in detail below.
(1) Culture of Microorganisms A standard strain of *Saccharomyces cerevisiae* was pre-cultured by shaking on GlyYP medium (Glycerol 2%, Yeast extract 0.5%, Peptone 1%), and the whole amount of the obtained culture was added to GlyYP medium and cultured by shaking.
(2) Method of Extracting and Purifying Total DNA.

In the extraction and purification processes of total DNA, a standard technique was adopted with some improvements such that: great attention should be given to the cleavage of mitochondrial DNA; enzyme treatment time should be reduced; stirring should be given gently; and so on. The detailed process is described as below.

From the *Saccharomyces cerevisiae* stain obtained by the above-stated culture (1), total DNA was extracted and purified according to the method described in Nobuo Ogawa:

Biochemistry Laboratory Procedure vol.39, Enzyme Molecular Genetics Laboratory Procedure (ed. Taiji Oshima), Japan Scientific Societies Press, p.84–85, 1996, and in Thomas D. Fox, Linda S. Folley, Julio J. Mulero, Thomas W. Mcmullin, Peter E. Thorsness, Lars O. Hedin and Maria C. Costanzo: *Guide to Yeast Genetics and Molecular Biology* (ed. Christine Guthrie, and Gerald R. Fink), Method in Enzymology 194, p.160–161, 1991.

EDTA, sodium phosphate and 2-mercaptoethanol were added to the *Saccharomyces cerevisiae* yeast, and zymolyase was further added thereto. Then, the mixture was heated to dissolve the cell wall of the *Saccharomyces cerevisiae* yeast. After that, EDTA, SDS and TrisHCl were added, and the mixture was lysed by heating. Then, potassium acetate was added to the lysed solution. After the mixture was gently stirred in order to avoid cleavage of mitochondrial DNA and fully mixed, it was cooled. After cooling, this dissolved solution was centrifuged, and the supernatant containing DNA was collected with a pipet. 2-propanol was added to the supernatant, then deposited DNA was picked up with a sterilized inoculating loop. The obtained DNA was fully dissolved in TE (1 mM EDTA, 10 mM Tris-HCl, pH7.4), and the precipitated insoluble substance was removed by centrifugation and only supernatant was collected. RNase A (10 mg/ul) and RNase T1 (0.5U/ul) were added to the collected supernatant to degradate coexisting RNA. This rough DNA solution was fractionated by the addition of solvent, and only the DNA layer was collected. After the collected DNA layer was purified by further addition of solvent, cooled ethanol was added thereto to precipitate DNA. Thus, purified DNA was prepared.

Up till now, in order to determine the nucleotide sequence of yeast mitochondrial DNA, highly purified mitochondrial DNA has been required, which was separated from nuclear DNA by ultracentrifugation or an equivalent means (Francoise Foury, Tiziana Roganti, Nicolas Lecrenier, and Benedicte Pernelle: The complete sequence of the mitochondrial genome of *Saccharomyces cerevisiae*, FEBS Letters 440, 325–331, 1998., Brigitte Weiss-Brummer, Alfred Zollner, Albert Haid, and Shahla Thompson: Mutation of a highly conserved base in the yeast mitochondrial 21S rRNA restricts ribosomal frameshifting, *Molecular and GeneralGenetics,* 248, 207–216, 1995., Jure PisKur, Sonja Smole, Casper Groth, Randi F Petersen, and Mogens B. Pedersen: Structure and genetic stability of mitochondrial genomes vary among yeasts of the genus Saccharomyces, *International Journal of Systematic Bacteriology,* 48, 1015–1024, 1998., Barnard Dujon: Sequence of the intron and flanking exons of the mitochondrial 21S rRNA gene of yeast strains having different alleles at the ω and rib-1 loci, *Cell,* 20, 185–197, 1980., Nobuo Ogawa et al.: *Biochemistry Laboratory Procedure* vol.39, Enzyme Molecular Genetics Laboratory Procedure (ed. Taiji Oshima), Japan Scientific Societies Press, p.84–85, 1996). Then, in order to determine the nucleotide sequence, in general, the obtained highly purified mitochondrial DNA has been cloned. In the present invention, however, the nucleotide sequence of yeast mitochondrial DNA was determined according to gene amplification technique (e.g. PCR), instead of the above standard techniques.

(3) Design of Primers for PCR on Mt-21S rDNA

There is not found any reports regarding the amplification of Mt-21S rDNA of *Saccharomyces cerevisiae* by PCR, and naturally there are also no reports regarding primers for PCR. Hence, consulting the known nucleotide sequence of Mt-21S rDNA (SEQ ID NO: 20), Mt-21S rDNA was divided into 7 fragments. Then, as shown in FIG. 2, primers for PCR (SEQ ID NOS: 1 to 16) capable of amplifying the DNA were designed.

Since yeast mitochondrial DNA consists of an overwhelming number of A (adenine) and T (thymine), usually comprising repeat sequences, it has been extremely difficult to find specific sequences having also an appropriate number of G (guanine) and C (cytosine) at adequate intervals. FIG. 2 shows sequences, which have relatively high specificity, have a relatively large number of G and C, and can be used as primers for PCR. For convenience of nucleotide sequence determination by DNA sequencer 377 (PE-ABI), these primers are designed to be divided into 7 fragments to carry out PCR for DNA comprising nucleotides 570 to 870. Moreover, since the nucleotide sequence of mitochondrial DNA comprises a large number of repeat sequences, it was inevitable that, in respect of some primers, 4 to 6 nucleotides of the 3'-terminus match with even those of regions other than a target region. However, for the reasons that it is possible to determine the nucleotide sequence with the primers shown in FIG. 2 by carrying out further analysis, and that there are no other appropriate sequences able to be used as primers, in the end, the primers shown in FIG. 2 were designed and applied.

(4) Amplification of Mt-21S rDNA (Mitochondrial 21S rRNA Gene) by PCR

Applying the above-purified DNA as a template, PCR was carried out using, as primers, SEQ ID NOS: 1 (−413F) and 2 (461R), SEQ ID NOS: 3 (64F) and 4 (690R), SEQ ID NOS: 5 (478F) and 6 (1290R), SEQ ID NOS: 7 (1048F) and 8 (1615R), SEQ ID NOS: 9 (1590F) and 10 (2258R), and SEQ ID NOS: 11 (1945F) (or SEQ ID NO: 12 (2269F)) and 13 (2676R), and SEQ ID NOS: 14 (2624F) (or SEQ ID NO: 15 (3889F)) and 16 (4457R) as primers, thereby amplifying Mt-21S rDNA. As a result, as shown in 1% agarose gel electrophoresis image in FIG. 1, the whole length of Mt-21S rDNA was amplified, divided into 7 regions, and thereby obtaining PCR product.

(5) Method of Determining the Nucleotide Sequence of PCR Product

The above PCR product DNA was subjected to DyeDeoxy reaction, using Bigdye terminater sequencing kit (PE-ABI) and primers used for the above PCR, and then the nucleotide sequence was determined with DNA sequencer 377 (PE-ABI). All of the 7 PCR products are double-stranded DNAs. The sequences of the main and complementary chains were determined, using a forward and a reverse primer for PCR, and primers specific for nucleotide sequence determination described in parentheses shown in FIG. 2, confirming that the sequences of these two chains matched.

The confirmation, connection and search of the obtained nucleotide sequences data were carried out with computer software: DNASIS (Hitachi Software Engineering Co., Ltd.)

The above-mentioned Fox et al., have reported that, where the nucleotide sequence of mitochondrial DNA (mitochondrial 21S ribosomal RNA was not described therein) is determined using DNA polymerase, restriction enzyme treatment for total DNA is required. According to Fox et al., this treatment is performed to decrease the viscosity of total DNA solution. However, in the present invention, even total DNA untreated with a restriction enzyme can be subjected to PCR with DNA polymerase. Therefore, in this respect also, the method of the present invention is superior to previous methods.

(6) Systematic Classification of *Saccharomyces cerevisiae* Strains Using the Determined Nucleotide Sequence of Mt-21S rDNA of *Saccharomyces cerevisiae*

Since the nucleotide sequences of Mt-21S rDNAs of 3 different types of *Saccharomyces cerevisiae* strains (IFO 10217 shown in SEQ ID NO: 18, IFO 10055 shown in SEQ ID NO: 17, and IFO 1998 shown in SEQ ID NO: 19), which were determined by the above method, are clearly distinct from each other (see FIG. 3A–3E), the present method was able to be applied to the phylogenetic classification of *Saccharomyces cerevisiae* strains. It took 4 days to determine the nucleotide sequence of a strain according to the present method.

EXAMPLE

The present invention is further described in the following examples. The example is provided for illustrative purposes only, and is not intended to limit the scope of the invention.

1. Test Strains

Standard strains of *Saccharomyces cerevisiae*, IFO 10217 (=ATCC 18824=NCYC505=JAM 14383=JCM 7255=CBS 1171), *S. cerevisiae* IFO 10055 (Basonym: *S. aceti* IFO 10055T), and *S. cerevisiae* IFO 1998 (Basonym: *S. oleaginosus* IFO 1998T) (T represents a standard strain).

2. Culture Method

Each of the test strains was precultured by shaking on 2.5 ml of GlyYP medium (Glycerol 2%, Yeast extract 0.5%, Peptone 1%) at 30° C. for 1 or 2 days, and the whole amount of the obtained culture was added to 50 ml of GlyYP medium and cultured by shaking for 2 days.

3. Method of Extracting and Purifying Total DNA

As a method of extracting and purifying total DNA of yeast, which enables the subsequent amplification of yeast mitochondrial DNA by PCR, an improved potassium acetate method was applied.

Consulting mainly the methods described by Ogawa, Fox et al., the extraction and purification was carried out as follows.

Each of the test strains cultured by the above method was centrifuged at 5,000 g for 5 minutes. The precipitated cells were washed once with sterilized distilled water to obtain 0.1 to 2 g (wet weight) of cells. 1 ml of 25 mM EDTA/50 mM sodium phosphate/pH7.5 and 10 $\mu$l of 2-mercaptoethanol were added to approx. 1 g of cells, and 300 units of zymolyase 60,000 (approx. 5 mg) was further added thereto. Then, the mixure was heated at 37° C. for 10 minutes to dissolve cell walls. After that, 1 ml of 80 mM EDTA/1% SDS/0.2M Tris HCl/pH9.5 was added and heated at 65° C. for 3 minutes to lyse. 700 $\mu$l of 5M potassium acetate corresponding to a quarter amount of lysate was further added, and the mixture was gently stirred in order to avoid cleavage of mitochondrial DNA and fully mixed. Then, the mixture was left on ice for 1 hour. After cooling, the mixture was centrifuged at 10,000 g for 10 minutes, and the supernatant containing DNA was collected with a pipet. To the supernatant, the equivalent amount of 2-propanol was added, and while gently stirring, deposited DNA was picked up with a sterilized inoculating loop. The obtained DNA was fully dissolved in 800 $\mu$l of TE (1 mM EDTA, 10 mM Tris-HCl, pH7.4), and the precipitated insoluble substance was removed by centrifugation at 10,000 g for 15 minutes to collect only the supernatant. 25 $\mu$l of RNase A (10 mg/ul) and 10 $\mu$l of RNase T1 (0.5U/ul) were added to the collected supernatant, and coexisting RNA was degraded by incubation at 37° C. for 20 minutes. To this rough DNA solution, an equivalent amount of 2-propanol was added, and while gently stirring, deposited DNA was picked up and dissolved in 400 $\mu$l of TE. To the DNA solution, the equivalent amount of phenol/chloroform/water (25:24:1) was added, and after fully mixing, the mixture was centrifuged at 5,000 rpm for 5 minutes and was divided into layers of DNA, coagulated protein and phenol. Only the DNA layer was collected and this was subjected to the same phenol treatment again. After the equivalent amount of chloroform was added to the collected DNA and fully mixed, the mixture was centrifuged at 5,000 rpm for 5 minutes and was divided into layers of DNA liquid and chloroform. Only the DNA liquid layer was collected and this was subjected to the same chloroform treatment again. After 2 volumes of cold ethanol was added to the obtained purified DNA liquid and slowly mixed, eluted DNA was precipitated by centrifugation at 5,000 rpm for 5 seconds. Only precipitated purified DNA was collected, dried and conserved at −20° C.

4. Design of Primers for PCR on Mt-21S rDNA

Since yeast mitochondrial DNA consists of an overwhelming number of A (adenine) and T (thymine), usually comprising repeat sequences, it has been extremely difficult to find some specific sequences having also an appropriate number of G (guanine) and C (cytosine) at adequate intervals. FIG. 2 shows sequences, which have relatively high specificity, have a relatively large number of G and C, and can be used as primers for PCR. For convenience of nucleotide sequence determination by DNA sequencer 377 (PE-ABI), these primers are designed to be divided into 7 fragments to carry out PCR for DNA comprising nucleotides 570 to 870. Moreover, since the nucleotide sequence of mitochondrial DNA comprises a large number of repeat sequences, it was inevitable that, in respect of some primers, 4 to 6 nucleotides of the 3'-terminus match with even those of regions other than a target region. However, for the reasons that it is possible to determine the nucleotide sequence with the primers shown in FIG. 2 by carrying out further analysis, and that there are no other appropriate sequences enable to be used as primers, in the end, the primers shown in FIG. 2 were designed and applied.

5. Amplification of Mt-21S rDNA (Mitochondrial 21S rRNA Gene) by PCR

Applying the purified total DNA of each test strain as a template, Mt-21S rDNA was amplified with the combined use of each of the forward and reverse primers for PCR shown in FIG. 2.

That is to say, using AmpliTaq DNA polymerase (Perkin-Elmer), according to established reaction conditions, there was prepared 50 $\mu$l of reaction solution containing a certain amount of 10×concentration buffer stock solution, 0.01 to 0.001 $\mu$g/$\mu$l purified total DNA used as a sample, 0.05 units/$\mu$l AmpliTaq polymerase, 0.2 mM dNTP, 0.3 pmol/$\mu$l forward and reverse primers, and 3 mM $MgCl_2$. After 50 $\mu$l of the reaction solution was put into a glass capillary, using 1605 type Air Thermo-Cycler (Idaho Technology), PCR was carried out 45 times, with temperature conditions set for DNA whose length corresponds to nucleotides 500 to 900. That is, after the solution was heated at 94° C. for 45 seconds, a cycle of reactions at 94° C. for 10 seconds for denaturation, at 55° C. for 15 seconds for annealing, and at 72° C. for 25 seconds for elongation was repeated for 45 cycles. After the reaction, PCR product DNA was purified with Centricon 100 (Amicon). The purified PCR product was subjected to 1% agarose gel electrophoresis to measure purity (see FIG. 1).

6. Method of Determining the Nucleotide Sequence of PCR Product

Approx. 10 to 30 ng of the above PCR product DNA was subjected to DyeDeoxy reaction, using a Bigdye terminater sequencing kit (Perkin-Elmer Applied Biosystems) and primers used for the above PCR, and then the nucleotide sequence was determined with DNA sequencer 377 (PE-ABI). All of the 7 PCR products are double-stranded DNAs. The sequences of the main and complementary chains were determined, using a forward and a reverse primer for PCR, and primers specific for nucleotide sequence determination described in parentheses shown in FIG. 2, confirming that the sequences of these two chains matched.

The confirmation, connection and search of the obtained nucleotide sequences data were carried out with DNASIS computer software (Hitachi Software Engineering Co., Ltd.) The nucleotide sequence of mitochondrial 21S ribosomal RNA of *Saccharomyces cerevisiae* IFO 10217, which was determined according to the above-stated method, is shown in SEQ ID NO:18. Similarly, those of *Saccharomyces cerevisiae* IFO 10055 and *Saccharomyces cerevisiae* IFO 1998 are shown in SEQ ID NOS:17 and 19, respectively.

7. Phylogenetic classification of *Saccharomyces cerevisiae* strains using the nucleotide sequence of each Mt-21S rDNA of *Saccharomyces cerevisiae* IFO 10217, *Saccharomyces cerevisiae* IFO 10055 and *Saccharomyces cerevisiae* IFO 1998.

FIG. 3 show the results of comparisons among the above-determined *Saccharomyces cerevisiae* strains shown in SEQ ID NOS: 17, 18 and 19. Shaded parts in FIG. 3 represent parts wherein the nucleotide sequences are matched in more than 2 strains of IFO 10217, IFO 10055 and IFO 1998.

By counting the number of relaxation nucleotides of transition type or transversion type among three strains in the parallel sequence listing shown in FIG. 3, and using the following formula proposed by Motoo Kimura, the respective evolutionary distance (Knuc) between strains was calculated:

$$Knuc = -\tfrac{1}{2}\log_e[(1-2P-Q)(1-2Q)^{1/2}]$$

wherein P denotes the substitution rate of transition type, and Q denotes that of transversion type.

Then, a dendrogram was made from the calculated evolutionary distance according to UPGMA (Unweighted pair-group method with arithmetric mean). FIG. 4 is a dendrogram showing the phylogenic relation among these three strains. This figure shows that the relation between IFO 10055 and IFO 1998 is more allied, on the other hand, the relation between these two strains and IFO 10217 is less allied. In FIG. 4, the concrete distance between two strains can be measured by the addition of the length of each crossbar of the two strains.

The method of the present invention does not need expensive instruments, ultracentrifuge nor restriction enzyme treatment, but it can reduce required time by a quarter to a half, when compared with previous methods. So, the nucleotide sequence determination method of the present invention is a simple, quick and excellent one. Furthermore, since the Mt-21S rRNA of each *Saccharomyces cerevisiae* strain is largely mutated, phylogenetic classification of *Saccharomyces cerevisiae* strains can also be performed using the above obtained nucleotide sequence.

SEQ ID NOS: 1 to 16 in Sequence Listing show primers.

SEQUENCE LISTING

<160> NUMBER OF SEQ ID NOS: 20

<210> SEQ ID NO 1
<211> LENGTH: 27
<212> TYPE: DNA
<213> ORGANISM: Artificial Sequence
<220> FEATURE:
<223> OTHER INFORMATION: PCR primer targeted to Mt-21S rRNA gene of
      Saccharomyces cerevisiae

<400> SEQUENCE: 1
caaaatagtc cgaccgaagg agatgag                                        27

<210> SEQ ID NO 2
<211> LENGTH: 27
<212> TYPE: DNA
<213> ORGANISM: Artificial Sequence
<220> FEATURE:
<223> OTHER INFORMATION: PCR primer targeted to Mt-21S rRNA gene of
      Saccharomyces cerevisiae

<400> SEQUENCE: 2
cttgctgacc cattatacaa aaggtac                                        27

<210> SEQ ID NO 3
<211> LENGTH: 24
<212> TYPE: DNA
<213> ORGANISM: Artificial Sequence
<220> FEATURE:
<223> OTHER INFORMATION: PCR primer targeted to Mt-21S rRNA gene of
      Saccharomyces cerevisiae

```
<400> SEQUENCE: 3
agatttaaag agataatcat ggag                                    24

<210> SEQ ID NO 4
<211> LENGTH: 20
<212> TYPE: DNA
<213> ORGANISM: Artificial Sequence
<220> FEATURE:
<223> OTHER INFORMATION: PCR primer targeted to Mt-21S rRNA gene of
      Saccharomyces cerevisiae

<400> SEQUENCE: 4
atagaaaacc agctatctgc                                         20

<210> SEQ ID NO 5
<211> LENGTH: 18
<212> TYPE: DNA
<213> ORGANISM: Artificial Sequence
<220> FEATURE:
<223> OTHER INFORMATION: PCR primer targeted to Mt-21S rRNA gene of
      Saccharomyces cerevisiae

<400> SEQUENCE: 5
gtaccttttg tataatgg                                           18

<210> SEQ ID NO 6
<211> LENGTH: 20
<212> TYPE: DNA
<213> ORGANISM: Artificial Sequence
<220> FEATURE:
<223> OTHER INFORMATION: PCR primer targeted to Mt-21S rRNA gene of
      Saccharomyces cerevisiae

<400> SEQUENCE: 6
cgttactcat gtcagcattc                                         20

<210> SEQ ID NO 7
<211> LENGTH: 22
<212> TYPE: DNA
<213> ORGANISM: Artificial Sequence
<220> FEATURE:
<223> OTHER INFORMATION: PCR primer targeted to Mt-21S rRNA gene of
      Saccharomyces cerevisiae

<400> SEQUENCE: 7
atgaacatgt aacaatgcac tg                                      22

<210> SEQ ID NO 8
<211> LENGTH: 26
<212> TYPE: DNA
<213> ORGANISM: Artificial Sequence
<220> FEATURE:
<223> OTHER INFORMATION: PCR primer targeted to Mt-21S rRNA gene of
      Saccharomyces cerevisiae

<400> SEQUENCE: 8
ctaacttatg agctatcttt gccgag                                  26

<210> SEQ ID NO 9
<211> LENGTH: 29
<212> TYPE: DNA
<213> ORGANISM: Artificial Sequence
<220> FEATURE:
<223> OTHER INFORMATION: PCR primer targeted to Mt-21S rRNA gene of
      Saccharomyces cerevisiae
```

```
<400> SEQUENCE: 9
caggtatgta agtagagaat atgaaggtg                                          29

<210> SEQ ID NO 10
<211> LENGTH: 27
<212> TYPE: DNA
<213> ORGANISM: Artificial Sequence
<220> FEATURE:
<223> OTHER INFORMATION: PCR primer targeted to Mt-21S rRNA gene of
      Saccharomyces cerevisiae

<400> SEQUENCE: 10
ctgataatga cgccccatca aaactac                                            27

<210> SEQ ID NO 11
<211> LENGTH: 28
<212> TYPE: DNA
<213> ORGANISM: Artificial Sequence
<220> FEATURE:
<223> OTHER INFORMATION: PCR primer targeted to Mt-21S rRNA gene of
      Saccharomyces cerevisiae

<400> SEQUENCE: 11
agtgaagatg ctatgtacct tcagcaag                                           28

<210> SEQ ID NO 12
<211> LENGTH: 25
<212> TYPE: DNA
<213> ORGANISM: Artificial Sequence
<220> FEATURE:
<223> OTHER INFORMATION: PCR primer targeted to Mt-21S rRNA gene of
      Saccharomyces cerevisiae

<400> SEQUENCE: 12
caatctctaa ttggtagttt tgatg                                              25

<210> SEQ ID NO 13
<211> LENGTH: 31
<212> TYPE: DNA
<213> ORGANISM: Artificial Sequence
<220> FEATURE:
<223> OTHER INFORMATION: PCR primer targeted to Mt-21S rRNA gene of
      Saccharomyces cerevisiae

<400> SEQUENCE: 13
ctagcgtaac ttttattcgt tatcaataac c                                       31

<210> SEQ ID NO 14
<211> LENGTH: 27
<212> TYPE: DNA
<213> ORGANISM: Artificial Sequence
<220> FEATURE:
<223> OTHER INFORMATION: PCR primer targeted to Mt-21S rRNA gene of
      Saccharomyces cerevisiae

<400> SEQUENCE: 14
cgagtgaaac aagtacgtaa gtatggc                                            27

<210> SEQ ID NO 15
<211> LENGTH: 27
<212> TYPE: DNA
<213> ORGANISM: Artificial Sequence
<220> FEATURE:
<223> OTHER INFORMATION: PCR primer targeted to Mt-21S rRNA gene of
      Saccharomyces cerevisiae

<400> SEQUENCE: 15
```

```
taagctmtgt ttgmcacctc gatgtcg                                         27
```

```
<210> SEQ ID NO 16
<211> LENGTH: 27
<212> TYPE: DNA
<213> ORGANISM: Artificial Sequence
<220> FEATURE:
<223> OTHER INFORMATION: PCR primer targeted to Mt-21S rRNA gene of
      Saccharomyces cerevisiae

<400> SEQUENCE: 16
ataaaggtgt gaaccaatcc cgcaagg                                         27

<210> SEQ ID NO 17
<211> LENGTH: 3315
<212> TYPE: DNA
<213> ORGANISM: Saccharomyces cerevisiae

<400> SEQUENCE: 17
tagtaaaaag tagaataata gatttgaaat atttattata tagatttaaa gagataatca       60
tggagtataa aaattaaatt taataaattt aatataacta ttaatagaat taggttacta      120
ataaattaat aacaattaat tttaaaacct aaaggtaaac ctttatatta ataatgtttt      180 tttttttaatt tttataatta agaataatta ttaataataa taaactaagt gaactgaaac    240
atctaagtaa cttaaggata ataaatcaac agagatatta tgagtattgg tgagagaaaa     300
taataaaggt ctaataagta ttatgtgaaa aaaatgtaag aaaataggat aacaaattct      360
aagactaaat actattaata agtatagtaa gtaccgtaag ggaaaatatg aaaatgatta     420
ttttataagc aatcatgaat atattatatt atattaatga tgtacctttt gtataatggg     480
tcagcaagta attaatatta gtaaaacaat aagttataaa taaatagaat aatatatata    540
tataaaaaaa tatattaaaa tatttaatta atattaattg acccgaaagc aaacgatcta    600
actatgataa gatggataaa cgatcgaaca ggttgatgtt gcaatatcat ctgattaatt    660
gtggttagta gtgaaagaca aatctggttt gcagatagct ggttttctat gaaatatatg    720
taagtatagc ctttataaat aataattatt atataatatt atattaatat tatataaaga    780
atggtacagc aattaatata tattagggaa ctattaaagt tttattaata atattaaatc    840
tcgaaatatt taattatata taataaagag tcagattatg tgcgataagg taaataatct    900
aaagggaaac agcccagatt aagatataaa gttcctaata aataaagt gaaataaata       960 ttaaaatatt ataatataat cagttaatgg gtttgacaat aaccattttt taatgaacat   1020
gtaacaatgc actgatttat aataaataaa aaaaaataat atttaaaatc aaatatatat   1080
atatttgtta atagataata tacggatctt aataataaga attatttaat tcctaatatg   1140
gaatattata ttttttataat aataataaga atataaatac tgaatatcta aatattatta   1200
ttactttttt ttaataataa taatatggta atagaacatt taatgataat atatattagt    1260
tattaattaa tatatgtatt aattaaatag agaatgctga catgagtaac gaaaaaaagg   1320
tataaacctt ttcacctaaa acataaggtt taactataaa agtacggccc ctaattaaat    1380
tatataagaa tataaatata tttaagatgg gataatctat attaataaaa atttatctta    1440
aaatatatat attattaata attatattaa ttaattaata atatatataa ttatattata    1500
tattatattt ttatatataa tatatataat ataaactaat aaagatcagg aaataattaa   1560
tgtataccgt aatgtagacc gactcaggta tgtaagtaga gaatatgaag gtgaattaga   1620
taattaaagg gaaggaactc ggcaaagata gctcataagt tagtcaataa agagtaataa   1680
```

-continued

```
gaacaaagtt gtacaactgt ttactaaaaa caccgcactt tgcagaaacg ataagtttaa      1740
gtataaggtg tgaactctgc tccatgctta atatataaat aaaattattt aacgataatt      1800
ttattaaatt taggtaaata gcagccttat tatgagggtt ataatgtagc gaaattcctt      1860
ggcctataat tgaggtcccg catgaatgac gtaatgatac aacaactgtc tccctttaa       1920 gctaagtgaa attgaaatcg tagtgaagat gctatgtacc ttcagcaaga cggaaagacc      1980
ctatgcagct ttactgtaat tagatagatc gaattattgt ttattatatt cagcatatta     2040
agtaatccta ttattaggta attgtttaga tattaatgag atacttatta taatataatg     2100
ataattctaa tcttataaat aattattatt attattatta ataataataa tatgctttca     2160
agcatagtga taaacatat ttatatgata atcactttac ttaatagata taattcttaa      2220
gtaatatata atatatatta tatatatatt atatataata taagagacaa tctctaattg     2280
gtagttttga tggggcgtca ttatcagcaa aagtatctga ataagtccat aaataaaaat     2340
ataaaattat tgaataaaaa aaataatata tattatatat attaattata aattgaaata     2400
tgtttatata aatttatatt tattgaatat atttttagtaa tagataaaaa tatgtacagt    2460
aaaattgtaa ggaaaacaat aataactttc tcctctctcg gtgggggttc acacctattt     2520
ttaataggtg tgaaccccctc ttcggggttc cggttccctt tcgggtcccg gaacttaaat    2580
aaaaatggaa agaattaaat taatataatg gtataactgt gcgataattg taacacaaac    2640
gagtgaaaca agtacgtaag tatggcataa tgaacaaata acactgattg taaaggttat    2700
tgataacgaa taaaagttac gctagggata acagggtaat ataacgaaag agtagatatt    2760
gtaagttatg tttgccacct cgatgtcgac tcaacatttc ctcttggttg taaaagctaa    2820
gaagggtttg actgttcgtc aattaaaatg ttacgtgagt tgggttaaat acgatgtgaa     2880
tcagtatggt tcctatctgc tgaaggaaat attatcaaat taaatctcat tattagtacg    2940
caaggaccat aatgaatcaa cccatggtgt atctattgat aataatataa tatatttaat    3000
aaaaataata ctttattaat atattatcta tattagttta tattttaatt atatattatc    3060
atagtagata agctaagttg ataataaata atattgaat acatattaaa tatgaagttg     3120
ttttaataag ataattaatc tgataatttt tactaaaat taataattat aggttttata     3180
tattatttat aaataaatat aatataataa taataattat tattattatt aataaaaaaa    3240
atattaatta taatattaat aaaatactaa tttatcagtt atctatataa tatctaatct    3300
attattctat atact                                                      3315
```

<210> SEQ ID NO 18
<211> LENGTH: 3272
<212> TYPE: DNA
<213> ORGANISM: Saccharomyces cerevisiae

<400> SEQUENCE: 18

```
tagtaaaaag tagaataata ggtttgaaat atttattata tagatttaaa gagataatca       60
tggagtataa aaattaaatt taataaattt aatataacta ttaatagaat taggttacta      120
ataaattaat aacaattaat tttaaaacct aaaggtaaac ctttatatta ataatgtttt      180 ttttttatttt tataattaag aataattatt aataataata aactaagtga actgaaacat     240
ctaagtaact taaggataat aaatcaacag agatattatg agtattggtg agagaaaata     300 ataaggtct aataagtatt atgtgaaaaa aatgtaagaa aataggataa caaattctaa      360
gactaaatac tattaataag tatagtaagt accgtaaggg aaagtatgaa aatgattatt     420
```

-continued

| | |
|---|---|
| ttataagcaa tcatgaatat attatattat attaatgatg tacctttttgt ataatgggtc | 480 |
| agcaagtaat taatattagt aaaacaataa gttataaata aatagaataa tatatatata | 540 |
| taaaaaaata tattaaaata tttaattaat attaattgac ccgaaagcaa acgatctaac | 600 |
| tatgataaga tggataaacg atcgaacagg ttgatgttgc aatatcatct gattaattgt | 660 |
| ggttagtagt gaaagacaaa tctggtttgc agatagctgg ttttctatga aatatatgta | 720 |
| agtatagcct ttataaataa taattattat ataatattat ataaatatta tataaagaat | 780 |
| ggtcacagcaa ttaatatata ttagggaact attaaagttt tattaataat attaaatctc | 840 |
| gaaatattta attatatata ataaagagtc agattatgtg cgataaggta aataatctaa | 900 |
| agggaaacag cccagattaa gatataaagt tcctaataaa taataagtga ataaatatt | 960 |
| aaatattat aatataatca gttaatgggt ttgacaataa ccatttttta atgaacatgt | 1020 |
| aacaatgcac tgatttataa taaataaaaa aaaataatat ttaaaatcaa atatatatat | 1080 |
| atttgttaat agataatata cggatcttaa taataagaat tatttaattc ctaatatgga | 1140 |
| atattatatt tttataataa taataaaaat ataaatactg aatatctaaa tattattatt | 1200 |
| actttttttt taataataat aatatggtaa tagaacattt aatgataata tatattagtt | 1260 |
| attaattaat atatgtatta attaaataga gaatgctgac atgagtaacg aaaaaaaggt | 1320 |
| ataaacctttt tcacctaaaa cataaggttt aactataaaa gtacggcccc taattaaatt | 1380 |
| atataagaat ataaatatat ttaagatggg ataatctata ttaataaaaa tttatcttaa | 1440 |
| aatatatata ttattaataa tttatattaat taattaataa tatatataat tatattatat | 1500 |
| attatatttt tatatataat atatataata taaactaata aagatcagga aataattaat | 1560 |
| gtataccgta atgtagaccg actcaggtat gtaagtagag aatatgaagg tgaattagat | 1620 |
| aattaaaggg aaggaactcg gcaaagatag ctcataagtt agtcaataaa gagtaataag | 1680 |
| aacaaagttg tacaactgtt tactaaaaac accgcacttt gcagaaacga taagtttaag | 1740 |
| tataaggtgt gaactctgct ccatgcttaa tatataaata aaattattta acgataattt | 1800 |
| tattaaattt aggtaaatag cagccttatt atgagggtta taatgtagcg aaattccttg | 1860 |
| gcctataatt gaggtcccgc atgaatgacg taatgataca acaactgtct cccctttaag | 1920 |
| ctaagtgaaa ttgaaatcgt agtgaagatg ctatgtacct tcagcaagac ggaaagaccc | 1980 |
| tatgcagctt tactgtaatt agatagatcg aattattgtt tattatattc agcatattaa | 2040 |
| gtaatcctat tattaggtaa tcgtttagat attaatgaga tacttattat aatataatga | 2100 |
| taattctaat cttataaata attattatta ttattattaa taataataat atgctttcaa | 2160 |
| gcatagtgat aaaacatatt tatatgataa tcactttact taatagatat aattcttaag | 2220 |
| taatatataa tatatattat atatatatta tatataaat aagagacaat ctctaattgg | 2280 |
| tagttttgat ggggcgtcat tatcagcaaa agtatctgaa taagtccata ataaaatata | 2340 |
| taaaattatt gaataaaaaa aataaatatat attatatata ttaattataa attgaaatat | 2400 |
| gtttatataa atttatattt attgaatata ttttagtaat agataaaaat atgtacagta | 2460 |
| aaattgtaag gaaaacaata ataactttct cctctctcgg tgggggttca cacctatttt | 2520 |
| taataggtgt gaaccctcc ttaaaaaata aaaatggaaa gaattaaatt aatataatgg | 2580 |
| tataactgtg cgataattgt aacacaaacg agtgaaacaa gtacgtaagt atggcataat | 2640 |
| gaacaaataa cactgattgt aaaggttatt gataacgaat aaaagttacg ctagggataa | 2700 |
| cagggtaata taacgaaaga gtagatattg taagttatgt ttgccacctc gatgtcgact | 2760 |
| caacatttcc tcttggttgt aaaagctaag aagggtttga ctgttcgtca attaaaatgt | 2820 |

-continued

| | |
|---|---|
| tacgtgagtt gggttaaata cgatgtgaat cagtatggtt cctatctgct gaaggaaata | 2880 |
| ttatcaaatt aaatctcatt attagtacgc aaggaccata atgaatcaac ccatggtgta | 2940 |
| tctattgata ataatataat atatttaata aaaataatac tttattaata tattatctat | 3000 |
| attagtttat attttaatta tatattatca tagtagataa gctaagttga taataaataa | 3060 |
| atattgaata catattaaat atgaagttgt tttaataaga taattaatct gataatttta | 3120 |
| tactaaaatt aataattata ggttttatat attatttata aatataatat aataattatt | 3180 |
| attattaata aaaaaaaata ttaattataa tattaataaa atactaattt atcagttatc | 3240 |
| tatataatat ctaatctatt attctatata ct | 3272 |

<210> SEQ ID NO 19
<211> LENGTH: 3303
<212> TYPE: DNA
<213> ORGANISM: Saccharomyces cerevisiae

<400> SEQUENCE: 19

| | |
|---|---|
| tagtaaaaag tagaataata gatttgaaat atttattata tagatttaaa gagataatca | 60 |
| tggagtataa aaattaaatt taataaattt aatataacta ttaatagaat taggttacta | 120 |
| ataaattaat aacaattaat tttaaaacct aaaggtaaac ctttatatta ataatgtttt | 180 |
| ttttttttat tttataatt aagaataatt attaataata ataaactaag tgaactgaaa | 240 |
| catctaagta acttaaggat aataaatcaa cagagatatt atgagtattg gtgagagaaa | 300 |
| ataataaagg tctaataagt attatgtgaa aaaaatgtaa gaaaatagga taacaaattc | 360 |
| taagactaaa tactattaat aagtatagta agtaccgtaa gggaaaatat gaaaatgatt | 420 |
| attttataag caatcatgaa tatattatat tatattaatg atgtaccttt tgtataatgg | 480 |
| gtcagcaagt aattaatatt agtaaaacaa taagttataa ataaatagaa taatatatat | 540 |
| atataaaaaa atatattaaa atatttaatt aatattaatt gacccgaaag caaacgatct | 600 |
| aactatgata agatggataa acgatcgaac aggttgatgt tgcaatatca tctgattaat | 660 |
| tgtggttagt agtgaaagac aaatctggtt tgcagatagc tggttttcta tgaaatatat | 720 |
| gtaagtatag cctttataaa taataattat tatataatat tatattaata ttatataaag | 780 |
| aatggtacag caattaatat atattaggga actattaaag ttttattaat aatattaaat | 840 |
| ctcgaaatat ttaattatat ataataaaga gtcagattat gtgcgataag gtaaataatc | 900 |
| taaagggaaa cagcccagat taagatataa agttcctaat aaataataag tgaaataaat | 960 |
| attaaaatat tataatataa tcagttaatg ggtttgacaa taaccatttt ttaatgaaca | 1020 |
| tgtaacaatg cactgatta taataaataa aaaaaaataa tatttaaaat caaatatata | 1080 |
| tatatttgtt aatagataat atacggatct taataataag aattatttaa ttcctaatat | 1140 |
| ggaatattat attttatata taataatata aatataaata ctgaatatct aaatattatt | 1200 |
| attactttt ttaataataa taatatggta atagaacatt taatgataat atatattagt | 1260 |
| tattaattaa tatatgtatt aattaaatag agaatgctga catgagtaac gaaaaaaagg | 1320 |
| tataaaccctt ttcacctaaa acataaggtt taactataaa agtacggccc ctaattaaat | 1380 |
| tatataagaa tataaatata tttaagatgg gataatctat attaataaaa atttatctta | 1440 |
| aaatatatat attattaata attatattaa ttaattaata atatatataa ttatattata | 1500 |
| tattatattt ttatatataa tatatataat ataaactaat aaagatcagg aaataattaa | 1560 |
| tgtataccgt aatgtagacc gactcaggta tgtaagtaga gaatatgaag gtgaattaga | 1620 |

-continued

```
taattaaagg gaaggaactc ggcaaagata gctcataagt tagtcaataa agagtaataa      1680
gaacaaagtt gtacaactgt ttactaaaaa caccgcactt tgcagaaacg ataagtttaa      1740
gtataaggtg tgaactctgc tccatgctta atatataaat aaaattatttt aacgataatt     1800
ttattaaatt taggtaaata gcagccttat tatgagggtt ataatgtagc gaaattcctt     1860
ggcctataat tgaggtcccg catgaatgac gtaatgatac aacaactgtc tcccctttaa     1920
gctaagtgaa attgaaatcg tagtgaagat gctatgtacc ttcagcaaga cggaaagacc     1980
ctatgcagct ttactgtaat tagatagatc gaattattgt ttattatatt cagcatatta     2040
agtaatccta ttattaggta atcgtttaga tattaatgag atacttatta taatataatg     2100
ataattctaa tcttataaat aattattatt attattatta ataataataa tatgctttca     2160
agcatagtga taaacatat ttatatgata atcactttac ttaatagata taattcttaa     2220
gtaatatata atatatatta tatatatatt atatataata aagagacaa tctctaattg      2280
gtagttttga tggggcgtca ttatcagcaa aagtatctga ataagtccat aaataaatat     2340
ataaaattat tgaataaaaa aaataatata tattatatat attaattata aattgaaata     2400
tgttttatata aatttatatt tattgaatat attttagtaa tagataaaaa tatgtacagt    2460
aaaattgtaa ggaaaacaat aataactttc tcctctctcg gtgggggttc acacctattt     2520
ttaataggtg tgaacccctc ttcggggttc cggttccctt tcgggtcccg gaacttaaat     2580
aaaaatggaa agaattaaat taatataatg gtataactgt gcgataattg taacacaaac     2640
gagtgaaaca agtacgtaag tatggcataa tgaacaaata acactgattg taaaggttat     2700
tgataacgaa taaaagttac gctagggata acagggtaat ataacgaaag agtagatatt    2760
gtaagttatg tttgccacct cgatgtcgac tcaacatttc ctcttggttg taaaagctaa    2820
gaagggtttg actgttcgtc aattaaaatg ttacgtgagt tgggttaaat acgatgtgaa    2880
tcagtatggt tcctatctgc tgaaggaaat attatcaaat taaatctcat tattagtacg    2940
caaggaccat aatgaatcaa cccatggtgt atctattgat aataatataa tatatttaat    3000
aaaaataata ctttattaat atattatcta tattagtttaa tatttttaatt atatattatc  3060
atagtagata agctaagttg ataataaata aatattgaat acatattaaa tatgaagttg    3120
ttttaataag ataattaatc tgataatttt tactaaaaat taataattat aggttttata    3180
tattatttat aaatataata taataattat tattattaat aaaaaaaaat attaattata    3240
atattaataa aatactaatt tatcagttat ctatataata tctaatctat tattctatat    3300
act                                                                    3303
```

<210> SEQ ID NO 20
<211> LENGTH: 4441
<212> TYPE: DNA
<213> ORGANISM: Saccharomyces cerevisiae

<400> SEQUENCE: 20

```
tagtaaaaag tagaataata gatttgaaat atttattata tagatttaaa gagataatca      60
tggagtataa taattaaatt taataaaattt aatataacta ttaatagaat taggttacta    120
ataaattaat aacaattaat tttaaaacct aaaggtaaac ctttatatta ataatgttat     180
tttttattat tttataata agaataatta ttaataataa taaactaagt gaactgaaac     240
atctaagtaa cttaaggata agaaatcaac agagatatta tgagtattgg tgagagaaaa    300
taataaaggt ctaataagta ttatgtgaaa aaaatgtaaa aaaataggat aacaaattct    360
aagactaaat actattaata agtatagtaa gtaccgtaag ggaaagtatg aaaatgatta    420
```

```
ttttataagc aatcatgaat atattatatt atattaatga tgtacctttt gtataatggg    480
tcagcaagta attaatatta gtaaaacaat aagttataaa taaatagaat aatatatata    540
tataaaaaaa tatattaaaa tatttaatta atattaattg acccgaaagc aaacgatcta    600
actatgataa gatggataaa cgatcgaaca ggttgatgtt gcaatatcat ctgattaatt    660
gtggttagta gtgaaagaca atctggtttt gcagatagct ggttttctat gaaatatatg    720
taagtatagc ctttataaat aataattatt atataatatt atattaatat tatataaaga    780
atggtacagc aattaatata tattagggaa ctattaaagt tttattaata atattaaatc    840
tcgaaatatt taattatata taataaagag tcagattatg tgcgataagg taaataatct    900
aaagggaaac agcccagatt aagatataaa gttcctaata aataaagt gaaataaata    960 ttaaaatatt ataatataat cagttaatgg gtttgacaat aaccattttt taatgaacat   1020
gtaacaatgc actgatttat aataaataaa aaaaataat atttaaaatc aaatatatat   1080
atatttgtta atagataata tacggatctt aataataaga attatttaat tcctaatatg   1140
gaatattata ttttataat aaaatataa atactgaata tctaaatatt attattactt   1200 ttttttttaat aataataata tggtaataga acatttaatg ataatatata ttagttatta   1260
attaatatat gtattaatta aatagagaat gctgacatga gtaacgaaaa aaaggtataa   1320 acctttttcac ctaaaacata aggtttaact ataaaagtac ggcccctaat taaattaata   1380
agaatataaa tatatttaag atgggataat ctatattaat aaaaatttat cttaaaatat   1440
atatattatt aataattata ttaattaatt aataatatat aaattatat tatatattat   1500 atattttta tataatataa actaataaag atcaggaaat aattaatgta taccgtaatg   1560
tagaccgact caggtatgta agtagagaat atgaaggtga attagataat taaagggaag   1620
gaactcggca agatagctc ataagttagt caataaagag taataagaac aaagttgtac   1680
aactgtttac taaaaacacc gcactttgca gaaacgataa gtttaagtat aaggtgtgaa   1740
ctctgctcca tgcttaatat ataaatacaaa ttatttaacg ataatttaat taaatttagg   1800
taaatagcag ccttattatg aggttataaa tgtagcgaaa ttccttggcc tataattgag   1860
gtcccgcatg aatgacgtaa tgatacaaca actgtctccc ctttaagcta agtgaaattg   1920
aaatcgtagt gaagatgcta tgtaccttca gcaagacgga aagacccat gcagctttac   1980 tgtaattaga tagatcgaat tattgtttat tatattcagc atattaagta atcctattat   2040
taggtaatcg tttagatatt aatgagatac ttattataat ataatgataa ttctaatctt   2100
ataaataatt attattatta ttattaataa taataatatg ctttcaagca tagtgataaa   2160
acatatttat atgataatca ctttacttaa tagatataat tcttaagtaa tatataatat   2220
atattttata tatattatat ataatataag agacaatctc taattggtag ttttgatggg   2280
gcgtcattat cagcaaaagt atctgaataa gtccataaat aaatatataa aattattgaa   2340
taaaaaaaaa ataatatata ttatatatat taattataaa ttgaaatatg tttatataaa   2400
tttatattta ttgaatatat tttagtaata gataaaaata tgtacagtaa aattgtaagg   2460
aaaacaataa taactttctc ctctctcggt gggggttcac acctatttt aataggtgtg   2520 aacccctctt cggggttccg gttccctttc gggtcccgga acttaaataa aaatggaaag   2580
aattaaatta atataatggt ataactgtgc gataattgta acacaaacga gtgaaacaag   2640
tacgtaagta tggcataatg aacaaataac actgattgta aaggttattg ataacgaata   2700
aaagttacgc tagggataat ttaccccctt gtcccattat attgaaaaat ataattattc   2760
```

| | |
|---|---|
| aattaattat ttaattgaag taaattgggt gaattgctta gatatccata tagataaaaa | 2820 |
| taatggacaa taagcagcga agcttataac aactttcata tatgtatata tacggttata | 2880 |
| agaacgttca acgactagat gatgagtgga gttaacaata attcatccac gagcgcccaa | 2940 |
| tgtcgaataa ataaaatatt aaataaatat caaaggatat ataaagattt ttaataaatc | 3000 |
| aaaaaataaa ataaaatgaa aaatattaaa aaaaatcaag taataaattt aggacctaat | 3060 |
| tctaaattat taaaagaata taaatcacaa ttaattgaat taaatattga acaatttgaa | 3120 |
| gcaggtattg gtttaatttt aggagatgct tatattcgta gtcgtgatga aggtaaacta | 3180 |
| tattgtatgc aatttgagtg aaaaaataag gcatacatgg atcatgtatg tttattatat | 3240 |
| gatcaatgag tattatcacc tcctcataaa aagaaagag ttaatcattt aggtaattta | 3300 |
| gtaattacct gaggagctca aacttttaaa catcaagctt ttaataaatt agctaactta | 3360 |
| tttattgtaa ataataaaaa acttattcct aataatttag ttgaaaatta tttaacacct | 3420 |
| ataagtttag catattgatt tatagatgat ggaggtaaat gagattataa taaaaattct | 3480 |
| cttaataaaa gtattgtatt aaatacacaa agttttactt ttgaagaagt agaatattta | 3540 |
| gttaaaggtt taagaaataa atttcaatta aattgttatg ttaaaattaa taaaaataaa | 3600 |
| ccaattattt atattgattc tataagttat ttaatttttt ataatttaat taaaccttat | 3660 |
| ttaattcctc aaatgatata taaattacct aatactattt catccgaaac tttttttaaaa | 3720 |
| taatattctt attttttattt tatgatatat ttcataaata tttatttata ttaaatttta | 3780 |
| tttgataatg atatagtctg aacaatatag taatatattg aagtaattat ttaaatgtaa | 3840 |
| ttacgataac aaaaaatttg aacagggtaa tatagcgaaa gagtagatat tgtaagctat | 3900 |
| gtttgccacc tcgatgtcga ctcaacattt cctcttggtt gtaaaagcta agaagggttt | 3960 |
| gactgttcgt caattaaaat gttacgtgag ttgggttaaa tacgatgtga atcagtatgg | 4020 |
| ttcctatctg ctgaaggaaa tattatcaaa ttaaatctca ttattagtac gcaaggacca | 4080 |
| taatgaatca acccatggtg tatctattga taataatata atatatttaa taaaaataat | 4140 |
| actttattaa tatattatct atattagttt atatttaat tatatattat catagtagat | 4200 |
| aagctaagtt gataataaat aaatattgaa tacatattaa atatgaagtt gtttaataa | 4260 |
| gataattaat ctgataattt tatactaaaa ttaataatta taggttttat atattattta | 4320 |
| taaataaata tattataata ataataatta ttattattaa taaaaaatat taattataat | 4380 |
| attaataaaa tactaatta tcagttatct atataatatc taatctatta ttctatatac | 4440 |
| t | 4441 |

What is claimed is:

1. A method for classifying a *Saccharomyces cerevisiae* strain which comprises the following steps:
   (a) determining the nucleotide sequence of a mitochondrial 21S ribosomal RNA gene of *Saccharomyces cerevisiae* of interest, and
   (b) comparing a nucleic acid with each of the positions selected from the group consisting of positions 22 of SEQ ID NO: 18, 186 of SEQ ID NO: 17, SEQ ID NO: 18 or SEQ ID NO: 19, 187 of SEQ ID NO: 17, SEQ ID NO: 18 or SEQ ID NO: 19, 188 of SEQ ID NO: 17, SEQ ID NO: 18 or SEQ ID NO: 19, 407 of SEQ ID NO: 18, 766 of SEQ ID NO: 8, 1170 of SEQ ID NO: 17, 1213 of SEQ ID NO: 17, SEQ ID NO: 18 or SEQ ID NO: 19, 1214 of SEQ ID NO: 17, SEQ ID NO: 18 or SEQ ID NO: 19, 2065 of SEQ ID NO: 17, 2582 of SEQ ID NO: 17, SEQ ID NO: 18 or SEQ ID NO: 19, 2583 of SEQ ID NO: 17, SEQ ID NO: 18 or SEQ ID NO: 19 and 2584 of SEQ ID NO: 17, SEQ ID NO: 18 or SEQ ID NO: 19 with a nucleic acid of the corresponding position(s) in other nucleotide sequences of a mitochondrial 21S ribosomal RNA gene of *Saccharomyces cerevisiae;* wherein the comparison at position 22 involves an A to G polymorphism; position 186 or 187 involves a deletion of the nucleic acid or T present at each position; position 188 involves a deletion of the nucleic acid or a substitution with an A or T; position 407 involves an A o G polymorphism; position 766 involves a T to A polymorphism; position 1213 involves a deletion of the nucleic acid or T present at the position; position 1214 involves a deletion of nucleic acid or T present at the position; position 2065 involves a C to T polymorphism; and positions 2582, 2583 and 2584 involve a deletion of the nucleic acid or A present at each position.

2. The method for classifying a *Saccharomyces cerevisiae* strain according to claim 1, wherein said step (a) includes a step of amplifying the nucleotide sequence of a mitochondrial 21S ribosomal RNA gene of *Saccharomyces cerevisiae* of interest using a set of primers selected from the group consisting of SEQ ID NOS: 1 to 16.

3. A method for classifying a *Saccharomyces cerevisiae* strain which comprises the following steps:
   (a) determining the nucleotide sequence of a mitochondrial 21S ribosomal RNA gene of *Saccharomyces cerevisiae* of interest, and
   (b) comparing a nucleic acid of positions 22, 186, 187, 188, 407, 766, 1170, 1213, 1214, 2065, 2582, 2583 and 2584 of SEQ ID NO: 17, 18 or 19 with a nucleic acid of the corresponding position(s) in other nucleotide sequences of a mitochondrial 21S ribosomal RNA gene of *Saccharomyces cerevisiae;*
      wherein the comparison at position 22 involves an A to G polymorphism in SEQ ID NO:18; position 186 involves a deletion of the nucleic acid in SEQ ID NO:17 or SEQ ID NO:18 or T present in SEQ ID NO:19; position 187 involves a deletion of the nucleic acid in SEQ ID NO:18 or T present in SEQ ID NO:17 or SEQ ID NO:19; position 188 involves a deletion in SEQ ID NO:18 or A present in SEQ ID NO:17 or T present in SEQ ID NO:19; position 407 involves an A to G polymorphism in SEQ ID NO:18; position 766 involves a T to A polymorphism in SEQ ID NO:18; position 1170 involves an A to G polymorphism in SEQ ID NO:17; position 1213 involves a deletion of the nucleic acid in SEQ ID NO:19 or T present at SEQ ID NO:17 or SEQ ID NO:18; position 1214 involves a deletion of the nucleic acid in SEQ ID NO:17 or SEQ ID NO:19 or T present in SEQ ID NO:18; position 2065 involves a C to T polymorphism in SEQ ID NO:17; and positions 2582, 2583 and 2584 involve a deletion of the nucleic acid in SEQ ID NO:17 or SEQ ID NO:19 or A present in SEQ ID NO:18.

* * * * *